(12) United States Patent
Shah

(10) Patent No.: US 8,050,776 B2
(45) Date of Patent: Nov. 1, 2011

(54) APPARATUS AND METHOD FOR ALLEVIATING NAUSEA

(76) Inventor: Kamlesh Shah, Burr Ridge, IL (US)

( * ) Notice: Subject to any disclaimer, the term of this patent is extended or adjusted under 35 U.S.C. 154(b) by 287 days.

(21) Appl. No.: 12/367,549

(22) Filed: Feb. 8, 2009

(65) Prior Publication Data

US 2009/0149921 A1 Jun. 11, 2009

Related U.S. Application Data

(63) Continuation of application No. 11/088,406, filed on Mar. 24, 2005, now Pat. No. 7,489,973.

(51) Int. Cl.
*A61N 1/04* (2006.01)
*A61N 1/08* (2006.01)
*A61H 39/00* (2006.01)

(52) U.S. Cl. ........................................ 607/149; 128/907

(58) Field of Classification Search .................. 606/129, 606/189, 204, 41–48; 600/548; 607/149, 607/150; 128/907
See application file for complete search history.

(56) References Cited

U.S. PATENT DOCUMENTS

| | | | |
|---|---|---|---|
| 4,981,146 A | 1/1991 | Bertolucci | |
| 6,361,550 B2 | 3/2002 | Grey | |
| 6,382,215 B1 | 5/2002 | Morrish | |
| 6,567,695 B1 | 5/2003 | Gruzdowich | |
| 2002/0156501 A1 | 10/2002 | Grey | |
| 2004/0172096 A1* | 9/2004 | Giuntoli et al. | 607/48 |

OTHER PUBLICATIONS

Kwang II Shin, Dong Soo Kim, Keon Sik Kim, Young Suk Kim. Effect of Electric Acupuncture Stimulation of PC 6 and PC 7 Antiemetic Point on Postoperative Nausea and Vomiting. Korean J Anestheisol Mar. 1995; 028(03): 433-439.*

* cited by examiner

*Primary Examiner* — Carl H. Layno
*Assistant Examiner* — Tammie K. Heller
(74) *Attorney, Agent, or Firm* — Ashok Tankha; Lipton, Weinberger & Husick

(57) ABSTRACT

A method and apparatus for prevention and treatment of nausea and vomiting by the simultaneous electrical stimulation of the pericardium meridian six point and pericardium meridian seven point on the ventral side of the wrist of a patient. The meridian stimulator comprises a wrist-band like housing that is worn on the ventral side of the human wrist and contains a circuitry means included within the said housing and electrically coupled to the electrodes. A negative electrode is positioned on the pericardium meridian six point and a positive electrode is placed on the pericardium meridian seven point and a low amperage current is passed through these points via electrodes positioned at these points. A liquid crystal display unit reads the current supplied to the electrodes and indicates via an indicator light when current is being supplied to the meridian stimulator and further comprises a touch screen for a power on and off button and for increasing the rate of electrical stimulations.

2 Claims, 6 Drawing Sheets

APPARATUS AND METHOD FOR ALLEVIATING NAUSEA

CROSS REFERENCE TO RELATED APPLICATIONS

This is a continuation application of U.S. patent application Ser. No. 11/088,406, filed on Mar. 24, 2005, now U.S Pat. No. 7,489,973, titled "Apparatus and method for alleviating nausea".

BACKGROUND

Nausea and vomiting are typically induced following the administration of general anesthesia and certain drugs, for example, narcotic pain alleviation and chemotherapy drugs. Also, conditions such as vertigo, dizziness, tinnitus, motion sickness and sea-sickness cause nausea. Anti-nausea remedies currently available in the market today include anti-nausea drugs, chemotherapy, acupuncture, acupressure and electro-acupuncture.

Stimulation of various areas on the body is known to be an effective treatment method for various medical conditions. Acupuncture and acupressure are existing Chinese therapeutic techniques that involve the stimulation of certain meridians and small, finite size points on the meridians known as acupuncture points. The current acupressure treatment for the alleviation of nausea and vomiting induced by general anesthesia, narcotic pain medications, chemotherapy, vertigo, dizziness, tinnitus and motion sickness consists of stimulation of an acupuncture point on the pericardium meridian known as the PC 6 point in a single therapeutic session.

Electro-acupuncture devices use non-invasive point stimulation whereby electricity is passed through two electrodes along the acupuncture meridians or channels. An example of an electro-acupuncture device is an electrode housed in a wrist-band that is positioned on the PC 6 acupuncture point and powered by a local battery to energise the PC 6 acupuncture point of the patient for the relief of nausea and vomiting. When administered properly, electro-acupuncture devices generally cause no physical injury to the patient and provide a non-chemical, non-invasive, painless and inexpensive method of alleviating nausea.

This invention comprises the stimulation of two acupuncture points on the pericardium meridian on the ventral side of the wrist known as the pericardium meridian six point (PC 6) and pericardium meridian seven point (PC 7) by the application of an electrically generated stimulus by a negative electrode positioned on the PC 6 point and a positive electrode positioned on the PC 7 point. The PC 6 acupuncture point is located on the pericardium meridian between the palmaris longus and flexor capri radialis tendons on the PC 3 and PC 7 line. The PC 7 point is located on the pericardium meridian at the middle of the wrist crease between palmaris longus and flexor capri radialis tendons. It was found that the simultaneous electrical stimulation of both PC 6 and PC 7 is much more effective for the prevention and treatment of nausea and vomiting compared to the stimulus of the area around only the PC 6 point.

DETAILED DESCRIPTION OF THE INVENTION

Figure 1:
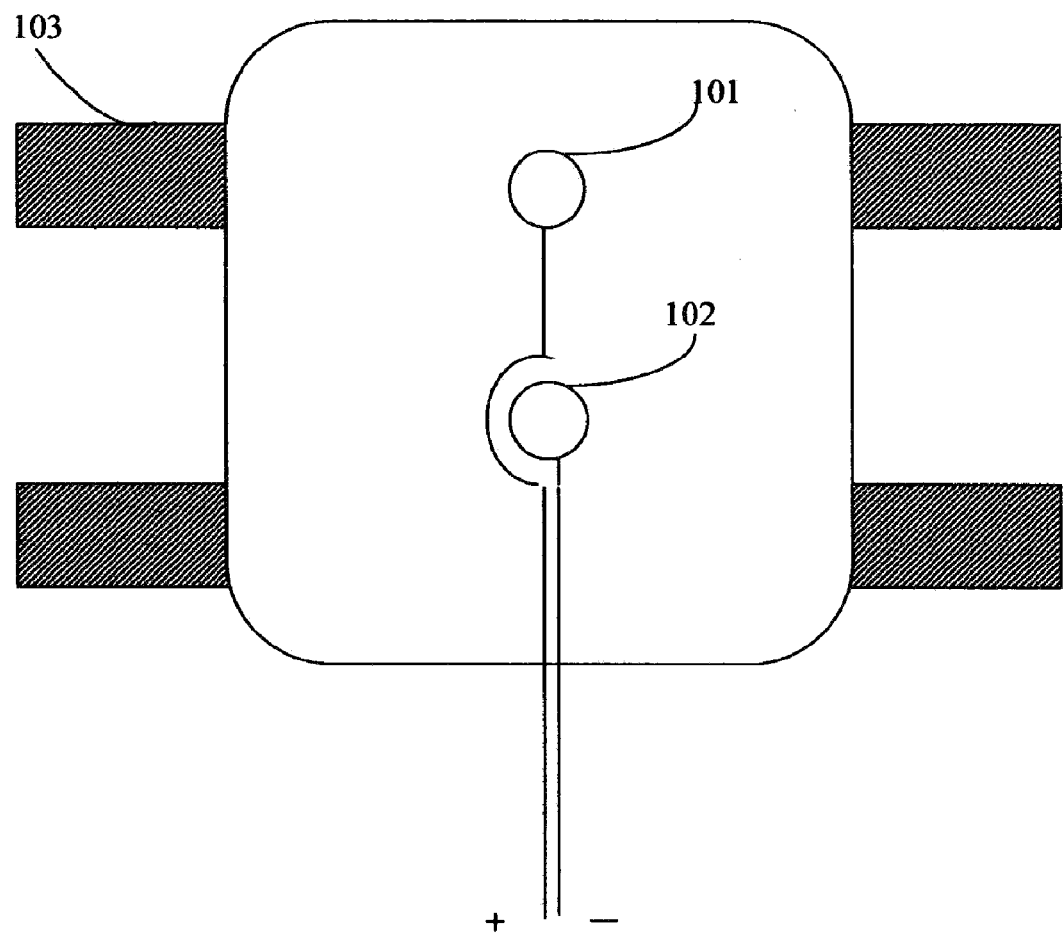
FIG. 1 illustrates the electrodes in the pericardium meridian stimulator for the prevention and treatment of nausea and vomiting.

FIG. 1 illustrates the position of the electrodes in the pericardium meridian stimulator 200 used for prevention and treatment of nausea and vomiting. The positive electrode 101 and the negative electrode 102 housed within the pericardium meridian stimulator 200 are powered by a local battery to provide a pulsed or a continuous electro-stimulation signal at the PC6 and PC 7 points.

The positive electrode 101 and negative electrode 102 are made of an electrically conducting material. In one embodiment of the invention, the electrodes are coated with a gel during manufacture of the pericardium meridian stimulator 200 and a removable plastic sheet is placed over the gel to hold the gel in place. Prior to the use of the pericardium meridian stimulator 200, the medical practitioner peels the plastic sheet off the electrodes 101 and 102 and positions the electrodes that are covered by a layer of gel on the pericardium meridian points PC b 6 and PC 7 on the wrist 303 of the patient. In another embodiment of the pericardium meridian stimulator, the gel is not provided with the electrodes during the assembly of the pericardium meridian stimulator 200 but is applied on the electrodes before the electrodes are positioned on the PC 6 and PC 7 points of the patient 303. The positive electrode 101 and the negative electrode 102 are electrically insulated from each other. The bottom of the pericardium meridian stimulator 200 is made of an electrically insulating material, for example, a plastic.

The spacing between the pericardium meridian six point (PC 6) 301 and pericardium meridian seven point (PC 7) 302 varies with age and body structure. To accommodate this variance, the present invention allows the relative movement and positioning of one electrode with respect to the other electrode along a guide or track in the housing of the pericardium meridian stimulator 200.

In one embodiment of the invention, the position of the positive electrode 101 is fixed with respect to the negative electrode 102 in the pericardium meridian stimulator with the position of negative electrode 102 adjustable along the longitudinal axis of the pericardium meridian defined by the line connecting points PC b 6 and PC 7. The positive electrode 101 is positioned on the PC 7 point 302 and the negative electrode 102 is positioned on the pericardium meridian six point (PC 6) 301 via a distance adjustment means, for example, a guide or track in the housing along which the negative electrode 102 can move.

In another embodiment of the invention, the position of the negative electrode 102 is fixed with respect to the positive electrode 101 in the pericardium meridian stimulator with the position of positive electrode 101 adjustable along the longitudinal axis of the meridian defined by the line connecting points PC 6 and PC 7. Electrode 102 is positioned on the PC 6 point 301 and the position of the positive electrode 101 is positioned on the pericardium meridian seven point (PC 7) 302 via a distance adjustment means, for example, a guide or track along which the positive electrode 101 can move.

The pericardium meridian stimulator 200 includes a wristband like housing that contains a strap 103 for strapping the pericardium meridian stimulator 200 onto the wrist of the patient. The housing of the pericardium meridian stimulator 200 which holds the electrodes and electrical circuitry is made of an electrically non-conductive material, for example, a plastic. The strap 103 is also made of an electrically non-conductive material. The strap 103 is flexible and is made of either adhesive packing or Velcro™, thereby allowing non-invasive contact of the pericardium meridian stimulator 200 with the body.

The positive electrode 101 and the negative electrode 102 are located on the lower surface of the pericardium meridian stimulator 200 and in indirect contact with the patient's skin through the gel medium. The positive electrode 101 and the negative electrode 102 are detachably attached to the housing. The battery 208 and the control electronics are located in the housing of the pericardium meridian stimulator 200. When electric power is supplied to the positive electrode 101 and to the negative electrode 102, the pericardium meridian points PC 6 301 and PC 7 302 are simultaneously stimulated.

The positive electrode 101 and the negative electrode 102 are each coupled via an electrical connector on the electrical circuit to the battery 208 located in the pericardium meridian stimulator 200. The electrically conducting sheath around the positive electrode 101 and the negative electrode 102 and the straps 103 are disposable. The electrically conducting sheath is fabricated from a polymer conducting material, for example a material comprising a metal bonded or impregnated to a polymer. In another embodiment of the invention, the sheath comprises a mesh or foil constructed of a high conductivity metal, for example silver, copper, etc. The LCD and electric circuit assembly are non-disposable.

Figure 2A:
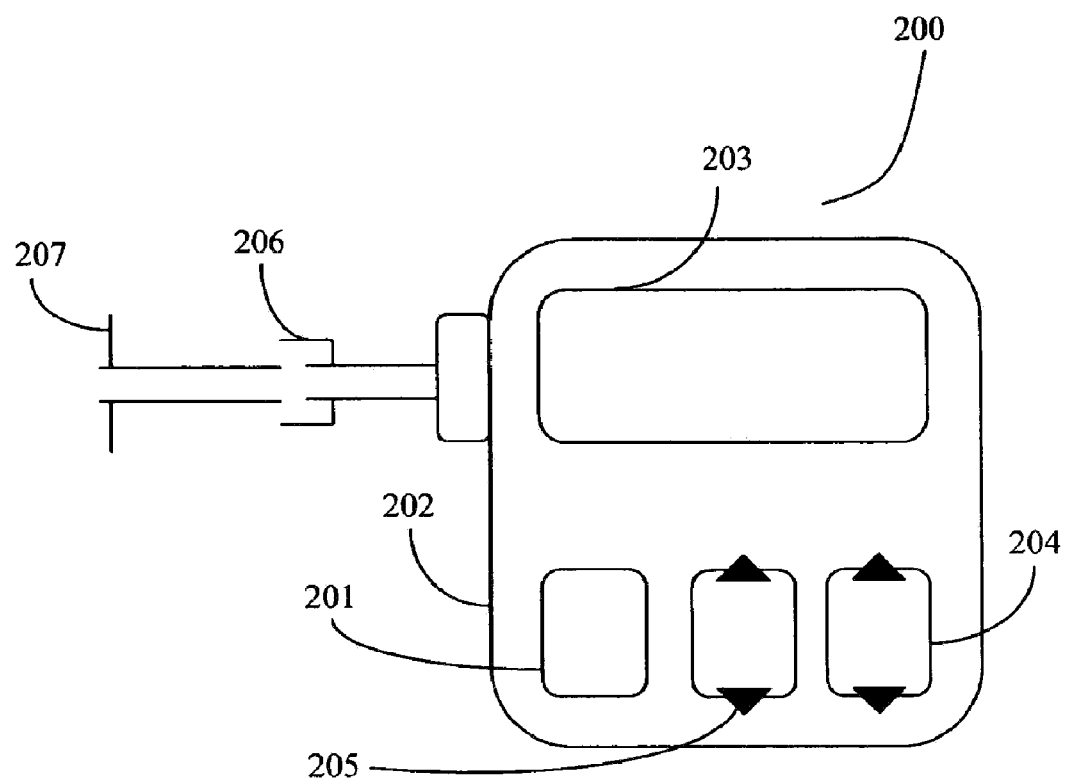
FIG. 2A illustrates the top view of the pericardium meridian stimulator when strapped on the ventral side of the patient's wrist.

FIG. 2A illustrates the top view of the pericardium meridian stimulator 200 as seen by the patient when the pericardium meridian stimulator is strapped onto the wrist of the patient. The pericardium meridian stimulator 200 is provided with a female connector 206 and male connector 207 for the wire-line connection from the battery to the electrodes, and a liquid crystal display (LCD) 203 read out located on the upper face of the pericardium meridian stimulator 200 in view of the patient. The LCD 203 displays the current supplied to the electrodes 101 and 102 and for indicating via an indicator light when electric power is being supplied to the electrodes 101 and 102. The LCD 203 touch screen 202 interface is provided with a power on-off button 201 and a switch 205 for increasing the electric pulse rate and thereby the electrical stimulation rate. The LCD 203 displays the current supplied to the electrodes. The power supplied to the electrodes 101 and 102 from the local battery is a low ampere, low voltage current, for example a 10, 20 or 30 milliampheres at 3 volts. The touch screen 202 button 204 increases or decreases the stimulus signal at the PC6 and PC 7 points by increasing or decreasing the current flow from the local battery to the electrodes 101 and 102. The LCD 203 also displays the pattern of current flowing between the electrodes, for example the electric pulse interval. The electric pulse rate is adjustable by an oscillator contained in the pericardium meridian stimulator 200 housing. The electric pulse rate can be adjusted by the patient or the medical practitioner using button 205 on the touch screen 202 from about 0.1 hertz to about 10 hertz For example, using button 205, the patient can set the cycle frequency at 1 hertz and receive a 1 pulse per second stimulus at the PC 6 point and the PC 7 point. The current flow through the electrodes 101 and 102 also produces an audible beep or click at the pericardium meridian stimulator. An audible disconnect alarm is provided in the electronic circuit of the pericardium meridian stimulator 200.

The electric circuit of the pericardium meridian 200 can output either a continuous current, or a pulsed current to the positive electrode 101 and the negative electrode 102 positioned at the PC 7 and PC 6 points respectively. The electrically insulated base of the pericardium meridian stimulator 200 and the electrically insulated material of the straps 105 ensure that the only path for the current flow in the now closed output circuit from the positive electrode 101 to the negative electrode 102 is through the flesh of the wrist along the pericardium meridian. In general, increasing the current amperage using button 204, or increasing the electric pulse rate using button 205 up to a certain point increases the anti-nausea effect of the invention.

Figure 2B:
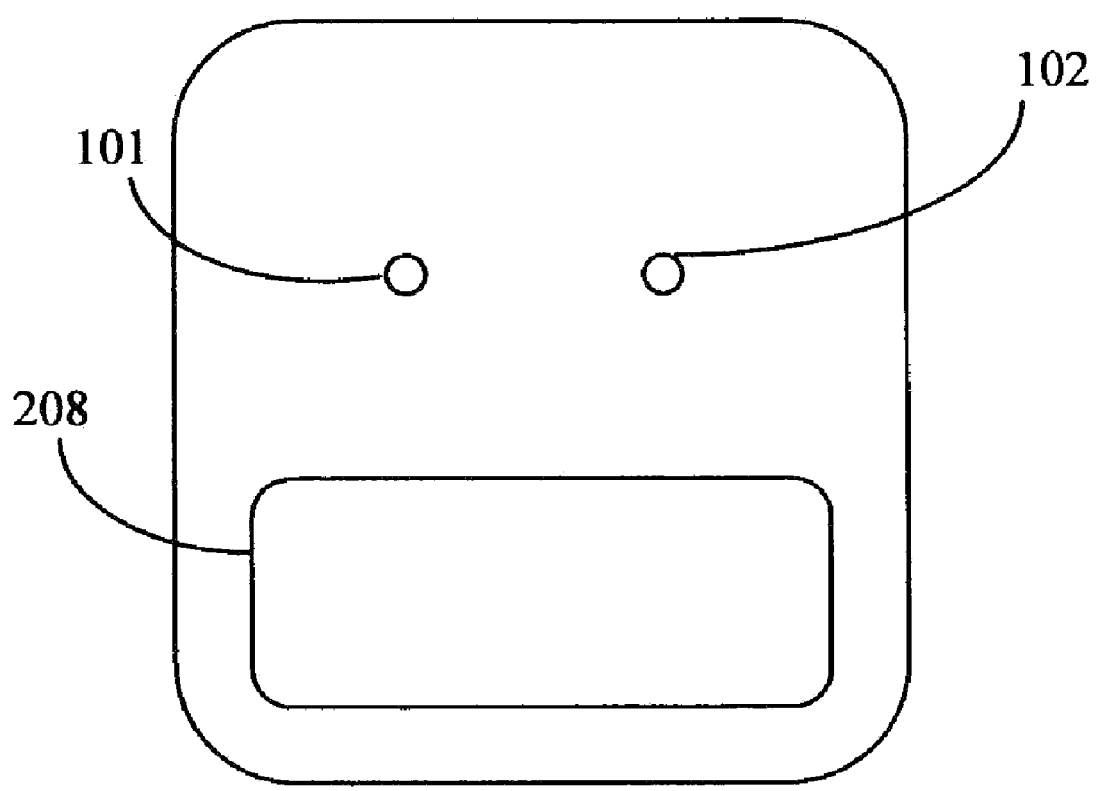
FIG. 2B illustrates the bottom view of the pericardium meridian stimulator. The bottom surface is in contact with the patient's wrist.

FIG. 2B illustrates the lower surface view of the pericardium meridian stimulator. The electrode assembly is detachably attached to the lower surface of the housing and is adapted for contact with the ventral side of the wrist of the patient. The electric circuitry in the pericardium meridian stimulator 200 is powered by the local battery source 208 located in the housing of the stimulator 200. The local battery 208 is a low voltage battery, for example, a 3 volt or 9 volt battery.

Figure 3:
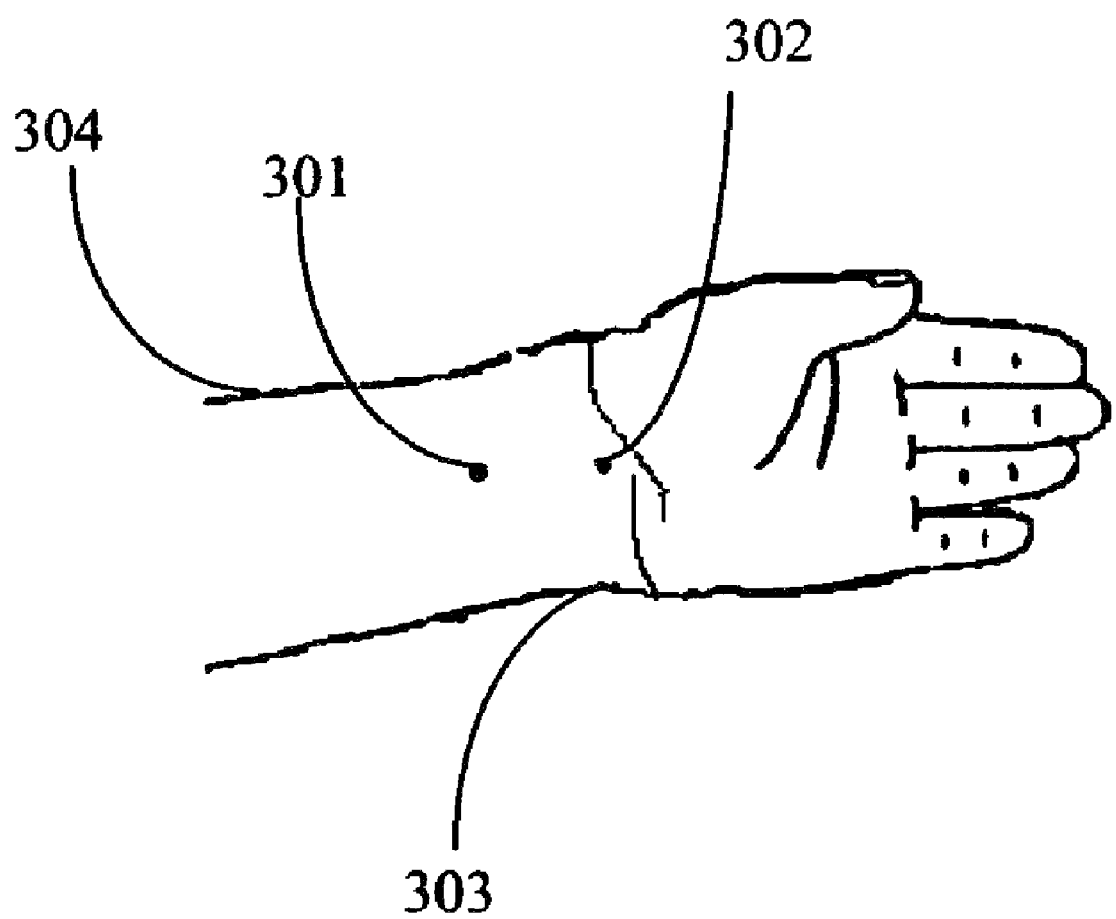
FIG. 3 illustrates the pericardium meridian six (PC 6) acupuncture point and pericardium meridian seven (PC 7) acupuncture point on the ventral side of the patient's wrist.

FIG. 3 illustrates the position of pericardium meridian six point 301 (PC 6) and the pericardium meridian seven point 302 (PC 7) on the ventral side of the patient's 304 wrist 303. The positive electrode 101 is positioned at the PC 7 point and the negative electrode 102 is positioned at the PC 6 point prior to passage of the electric power through the electrodes.

Figure 4:
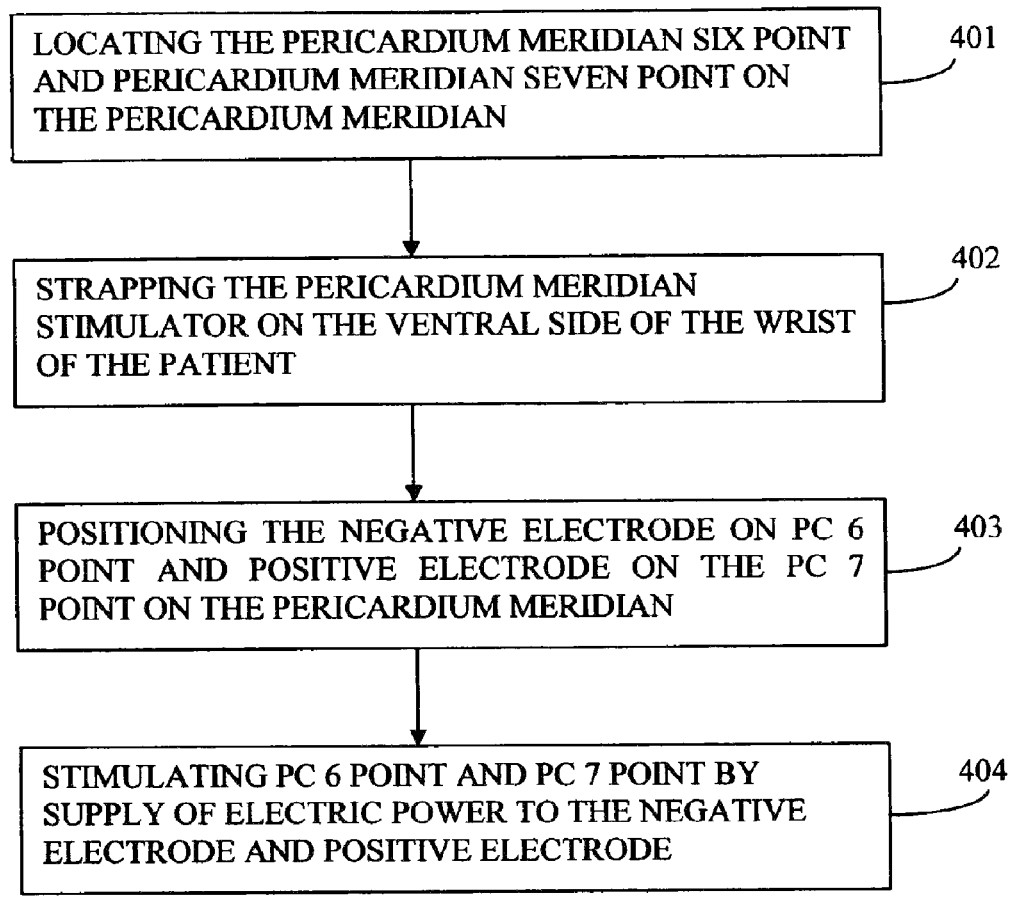
FIG. 4 illustrates the method of applying electro-acupuncture at the PC 6 and PC 7 pericardium meridian acupuncture points.

FIG. 4 illustrates the method of applying electro-acupuncture at the pericardium meridian six point and the pericardium meridian seven point. The pericardium meridian six point and the pericardium seven point are located on the ventral side of the patient's 304 wrist 303. The pericardium meridian stimulator is strapped 402 onto the wrist 303 of the patient 304. The negative electrode 102 is positioned 403 on the pericardium meridian point six and the positive electrode 101 is positioned 403 on the pericardium meridian seven point by adjusting the distance between the electrodes along a guide or track housed in the wrist band housing. A continuous or pulsed current of selected amplitude is applied to the positive electrode 101 and to the negative electrode 102, whereby the pericardium six point (PC 6) and the pericardium seven point (PC 7) are simultaneously stimulated 404 along the pericardium meridian.

Figure 5:
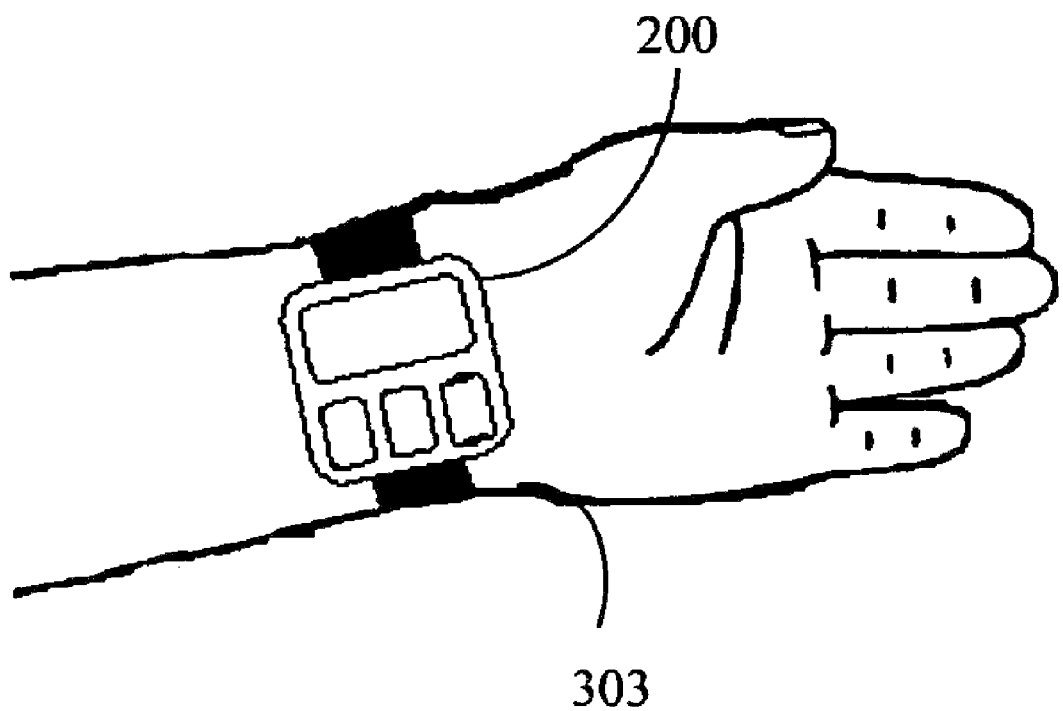
FIG. 5 illustrates the position of the pericardium meridian stimulator device on the ventral side of the patient's wrist.

FIG. 5 illustrates the pericardium meridian stimulator 200 strapped on the ventral side of the patient's wrist 303. The simultaneous electrical stimulation of both the PC 6 point 301 and PC 7 point 302 is much more effective in prevention and treatment of nausea and vomiting compared to the stimulus of only one point, such as PC 6 301. The simultaneous stimulation of both PC 6 301 and PC 7 302 helps in the prevention and treatment of nausea and vomiting induced by general anesthesia and by medication, for example, narcotic pain alleviation drugs and chemotherapy. The pericardium meridian stimulator system of this invention can also be used to treat vertigo, dizziness, tinnitus, motion sickness and similar conditions.

The simultaneous electro-stimulation procedure at the PC 6 and PC 7 acupuncture point, described above, has been used to effectively treat patients considered high risk for post-operative nausea and vomiting, for example, in procedures such as laparoscopies, sinus surgeries, thyroidectomy, etc.

The simultaneous PC 6 and PC 7 electro-stimulation procedure of this invention has also been used to treat patients who have a history of severe post-operative nausea and vomiting after receiving general anesthesia, and for patients who developed severe post-operative nausea and vomiting in the post-anesthetic recovery room and failed to respond to conventional medical therapies, for example the administration of drugs such as Metoclopromide and/or Ondansetron.

I claim:

1. A method of applying electro-acupuncture at a pericardium meridian six point and a pericardium meridian seven point of an individual for controlling nausea, comprising:

locating said pericardium meridian six point and said pericardium meridian seven point on a ventral side of a wrist of said individual;

strapping a pericardium meridian stimulator onto said wrist of the individual;

positioning a negative electrode of said pericardium meridian stimulator on said pericardium meridian six point on the wrist of the individual;

positioning a positive electrode of the pericardium meridian stimulator on the pericardium meridian seven point on the wrist of the individual by adjusting the distance of said positive electrode from said negative electrode along a guide track;

selecting an amplitude of electrical power and a pulse rate for delivering said electrical power to the positive electrode and the negative electrode of the pericardium meridian stimulator; and applying said electro-acupuncture by applying the electrical power at said selected amplitude and said selected pulse rate to the positive electrode and the negative electrode of the pericardium meridian stimulator;

whereby the pericardium six point and the pericardium seven point are simultaneously stimulated along the pericardium meridian for controlling nausea in the individual.

2. A method of controlling nausea in an individual by applying electro-acupuncture using a pericardium meridian stimulator at a pericardium meridian six point and a pericardium meridian seven point, said method comprising:

strapping a pericardium meridian stimulator onto a wrist of the individual, wherein said pericardium meridian stimulator comprises a positive electrode and a negative electrode;

positioning the negative electrode on said pericardium meridian six point on the wrist of the individual and the positive electrode on the pericardium meridian seven point on the wrist of the individual by adjusting the distance of said positive electrode from said negative electrode along a guide track of said pericardium meridian stimulator; and applying said electro-acupuncture by applying an electrical power to the positive electrode and the negative electrode of the pericardium meridian stimulator;

whereby the pericardium six point and the pericardium seven point are simultaneously stimulated along the pericardium meridian for controlling nausea in the individual.

\* \* \* \* \*